United States Patent [19]
Echerer

[11] Patent Number: 5,801,755
[45] Date of Patent: Sep. 1, 1998

[54] INTERACTIVE COMMUNCIATION SYSTEM FOR MEDICAL TREATMENT OF REMOTELY LOCATED PATIENTS

[76] Inventor: Scott J. Echerer, 428 Lafayette Ave., Cayce, S.C. 29033

[21] Appl. No.: 629,506

[22] Filed: Apr. 9, 1996

[51] Int. Cl.$^6$ .................................................. H04N 7/14
[52] U.S. Cl. .................................. 348/13; 348/17; 348/15
[58] Field of Search ..................................... 348/13, 17, 18, 348/15, 7, 8, 1, 14; H04N 7/14

[56] References Cited

U.S. PATENT DOCUMENTS

| | | | |
|---|---|---|---|
| 3,566,370 | 2/1971 | Worthington, Jr. et al. | 340/172.5 |
| 4,722,349 | 2/1988 | Baumberg | 128/904 X |
| 5,339,821 | 8/1994 | Fujimoto | 128/700 |
| 5,390,238 | 2/1995 | Kirk et al. | 379/93 |
| 5,393,964 | 2/1995 | Hamilton et al. | 128/381 |
| 5,441,047 | 8/1995 | David et al. | 128/670 |
| 5,462,051 | 10/1995 | Oka et al. | 128/630 |
| 5,482,043 | 1/1996 | Zulauf | 128/660.04 |
| 5,562,550 | 10/1996 | Chartrand | 473/131 |
| 5,594,789 | 1/1997 | Seazholtz et al. | 348/13 |
| 5,596,994 | 1/1997 | Bro | 128/732 |
| 5,613,012 | 3/1997 | Hoffman et al. | 382/115 |

Primary Examiner—Tommy P. Chin
Assistant Examiner—Nhon T. Diep
Attorney, Agent, or Firm—Michael A. Mann

[57] ABSTRACT

A system for providing medical services to a patient at a location remote to a medical practitioner comprises a patient's station and a medical practitioner's station in communication with each other. Both stations are equipped with video and audio capability allowing both the practitioner and patient to see and hear one another. A variety of devices are present at both stations that enable the transmission of information between the parties. Several monitors, located at the patient's station, enable the practitioner to measure and monitor several health related parameters. A camera is mounted in the patient's station in front of a frame that holds the patient's driver's license or other forms of identification. Images of the patient's identifying documents are transmitted to the medical practitioner station to allow positive identification. Payment for medical services rendered is accomplished by using a credit card reader in the patient's station, supplying an accepted insurance card, or by obtaining an account number from the retailer who on whose premises the patient's station is located.

13 Claims, 2 Drawing Sheets

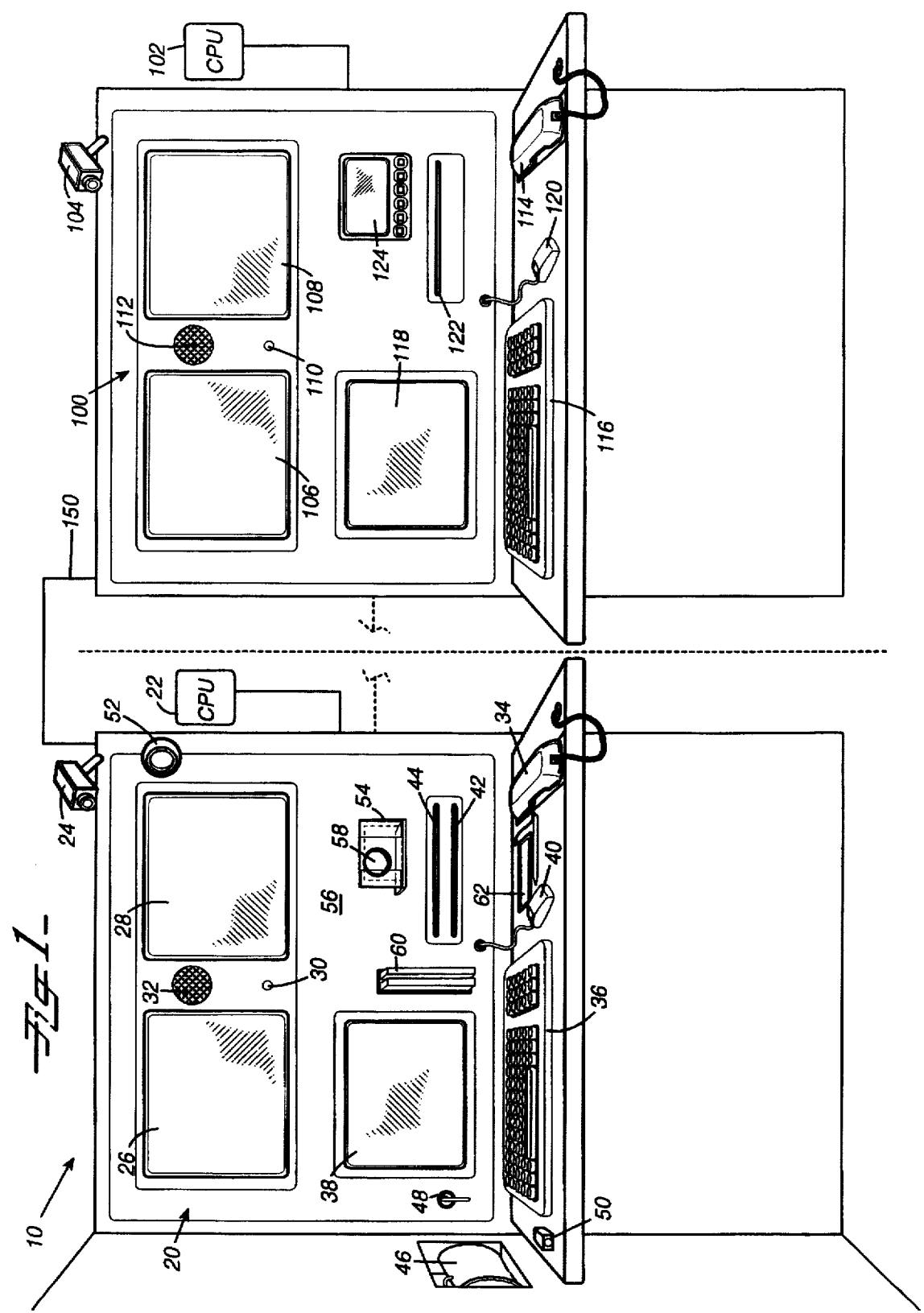

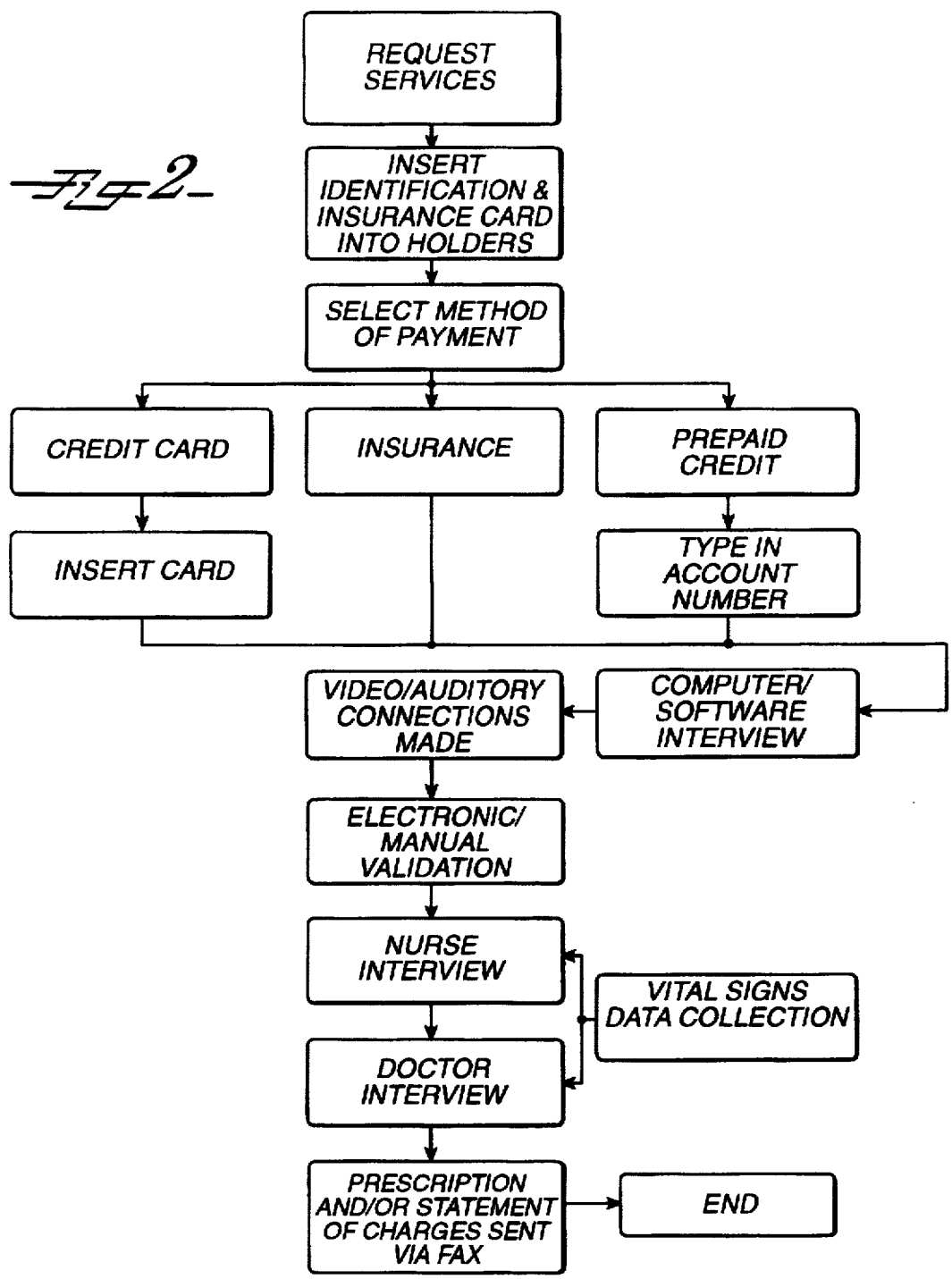

INTERACTIVE COMMUNCIATION SYSTEM FOR MEDICAL TREATMENT OF REMOTELY LOCATED PATIENTS

BACKGROUND OF THE INVENTION

1. Field of the Invention

The present invention relates generally to diagnosis and treatment of patients. More particularly, the present invention is a system for enabling medical treatment to be given to a patient at a remote location by a medical practitioner from a central location.

2. Discussion of Background

Not all patients that visit the hospital or their doctor's office are in need of highly specialized medical care. Many times, a patient needs only general medical advice or a prescription for medication to treat a common cold, a minor rash, or simple infection. In many instances, a patient must schedule a visit to the doctor for nothing more than the renewal of a prescription.

The necessity of scheduling a doctor's appointment and visiting the office during normal working hours is an inconvenience to the patient who must leave work to see the doctor. This inconvenience is compounded by the long waiting periods often encountered in doctors' offices. Often, due to these inconveniences, the patient will forgo seeking medical attention for minor ailments. Unfortunately, if not properly treated, many minor ailments will grow into serious medical problems that require immediate, and costly, medical attention.

Consequently, there exists a need for a medical communications system which can deliver basic medical care in a cost efficient manner.

SUMMARY OF THE INVENTION

According to its major aspects and briefly stated, the present invention is an interactive communication system enabling a doctor or other health care workers at a central station to provide basic medical attention to a patient at a remote station in another location. The communications system comprises a remote station, normally the patient's station, and a central or medical practitioner's station. The term "patient," as used herein, broadly means any individual that is in need of medical attention while the term "medical practitioner" means a physician, nurse, pharmacist or other medical practitioner trained and licensed for providing the medical service performed using the present system. It will be clear that higher levels of service may be provided by medical practitioners who meet the necessary qualifications for providing that service.

The first station is equipped with a video camera and two video terminals, or one video terminal with several images simultaneously displayed. The first terminal displays a live video image of the medical practitioner. The second terminal displays the patient so he or she can see the image that is being transmitted. Both remote and central stations contain a speaker and a microphone. Alternatively or in addition, telephone headsets are provided, allowing private conversation between the practitioner and patient.

To enable sending and receiving text, a computer keyboard and screen, and a facsimile machine are located in each station. Other types of input devices, such as a mouse for control of the position of the cursor or pointer present on the screen or a touch screen technology can be used as well. A variety of diagnostic devices are also present at the patient's station for measuring and monitoring health parameters such as temperature, heart rate, and blood pressure.

An additional camera, located within the interior of the patient's station, is directed towards a frame recessed in the station wall. The frame is dimensioned to receive an insurance card, driver's license or other identification cards of similar dimension. The video image of the card is converted to a still image by a video camera or a scanner and transmitted to the central station. As a result, the practitioner at the central station can verify the identity of the patient requesting medical attention by comparing the picture on the identification card or the number on an insurance card to records available to the medical practitioner. More sophisticated identification techniques can be used in lieu of these or in addition to these.

Establishing a mode of payment for services rendered can be accomplished in several ways. First, the patient may already have established an account with the medical practitioner and, by simply requesting a bill against that account, the arrangements are complete. If there is no existing arrangement, the patient may pay by credit (or debit) card. In the remote station, a credit card reader and an electronic signature device are housed for the reading of credit card information and signing an electronic receipt. Alternatively, if the remote station is located at a pharmacy or other place where the owner of the premises can provide credit to the patient, the patient may charge its bill to an account number provided by the owner. Upon conclusion of the session between practitioner and patient, an itemized bill would be forwarded to the patient's station by facsimile. A monthly statement of services rendered from that station would be mailed to the owner of the premises. Additionally, patient's could pay using a HMO, PPO, or similar health management program card. With this mode of payment, the card is placed within the frame while its image is forwarded to the practitioner's station, as discussed above.

Each station is controlled by a central processing unit (CPU). Audio/video signals and data are transmitted between stations using established telecommunication methods and systems, including radio or microwave transmission to distant receivers, perhaps via satellites, and modems in combination with telephone lines or fiber optic cables.

The patient's station may be installed in any pharmacy, drugstore or large supermarkets having a pharmacy. Additionally, the station may also be located in airports, malls, or corporations which seek to provide on site medical attention for their employees. Moreover, many hospitals will install a station to allow sophisticated diagnoses of patients by specialists located in distant cities. With a station located at a small clinic, manned only by a nurse trained to provide routine health care, such as the administration of inoculations, for example, assisted by a doctor at the remote station, health care can be provided to those in small communities or rural areas more efficiently.

The incorporation of devices which make possible both the positive identification of the patient and a method of payment for medical services rendered is an important feature of the present invention. Although the importance of proper identification of a patient for treatment purposes will be clear, the importance of patent identification for securing payment and the need to have some way of securing payment cannot be disregarded. Medical services are expensive, and patients are expected to pay for them. By providing for these, the present invention enables remote, interactive providing of medical services to be given in a variety of important circumstances, ranging from diagnosis of simple ailments to customers at a pharmacy, to making sophisticated diagnosis of a patient located in another city. Furthermore, these services can be provided at much lower cost than presently because they eliminate much of the inefficiency of the present system.

Establishing a two way interactive communication capability is another feature of the present invention. This capability eliminates the need for the patient to be literally "face to face" with the medical practitioner for medical services to be rendered. As a result, substantial savings can be realized by both practitioner and patient. Patients whose ailments are simple can be quickly diagnosed, at all hours of the day, without having to take the time to go to the doctor's office or hospital. Moreover, the use of doctors' time can be maximized because they can examine and treat a series of patients in rapid succession from one location. Furthermore, in rural areas that are underserved by doctors, patients often allow medical conditions to go untreated because of the difficulty and inconvenience in traveling long distances in order to obtain medical attention. The present invention can be used to set up a series of satellite clinics, enabling doctors at distant locations to provide much needed medical care.

The ability to measure and monitor a variety of different medical variables is still another feature of the present invention. By monitoring such variables it is possible to make a more accurate diagnosis of the patient. In addition, as technology develops, new, less invasive, methods and apparatus for analyzing physical and chemical aspects of the body that impact health, such apparatus may be incorporated into the present invention. For example, sound waves can be passed through the body and the echoes analyzed in lieu of the current subjective technique of palpation. Consequently, more sophisticated and wide ranging diagnosis can be made.

Other features and their advantages will be apparent to those skilled in the art from a careful reading of the Detailed Description of Preferred Embodiments accompanied by the following drawings.

BRIEF DESCRIPTION OF THE DRAWINGS

In the drawings,

FIG. 1 is a front view of a medical communications system according to a preferred embodiment of the present invention; and FIG. 2 is a flow chart depicting the major steps of a medical communication system according to a preferred embodiment of the present invention.

DETAILED DESCRIPTION OF PREFERRED EMBODIMENTS

The present invention is a medical communications system that enables medical care to be given by a medical practitioner present at a central station to a patient present at a remote location. The present invention allows the two to communicate live, seeing and hearing each other, and to transmit information and data for the diagnosis and treatment of the patient's condition without the need for face-to-face examination. Additionally, the system incorporates technology to allow positive identification of the patient, and establishment of a mode of payment for services rendered.

Referring now to FIG. 1., there is shown a medical communications system according to a preferred embodiment of the present invention, generally designated by reference numeral 10. System 10 is comprised of a remote, or patient's station 20, remotely located from a central or practitioner's station 100. Stations 20 and 100 are electronically connected via communications link 150. Each station 20 and 100 is equipped with a central processing unit 22 and 102 respectively, which controls the instructions, provides the software, and manages the data transmission between station 20 and station 100. To provide increased privacy patient's station 20 may be enclosed in a booth (not shown).

To enable video conferencing between the practitioner and patient, both station 20 and 100 contain a video camera 24, 104, a pair of video terminals, 26, 28 and 106, 108. Alternatively, a simple video terminal capable of displaying multiple images using standard split screen technology can be substituted. In each station, one video terminal (26 and 106) displays the individual present at the opposing station. The other terminal (28 and 108) displays the individual seated within the station. Consequently, each individual is capable of viewing the video image of themselves that is being conveyed to the opposing station. Obviously, having only one monitor, limited to seeing the party on the other end would be possible even without split screen; however, for feedback as to what the other party is seeing, the preferred embodiment of the present invention includes two monitors. Audio communication is accomplished by microphones 30 and 110 and speakers 32 and 112, enabling the practitioner and patient to talk freely. Alternatively, telephones receivers 34 and 114 can be used to permit more private conversation between the two participants.

Textual information between the parties is conveyed using computer keyboards 36, 116 and their dedicated terminals 38, 118. Electronic cursor directors 40 and 120, commonly referred to as a "mouse" are present at both stations 20 and 100 to further facilitate the transfer of information between the parties. CPU's 22 and 102 control the operation of keyboard, mouse and dedicated terminals at their respective locations.

Station 20 is also equipped with a printer 42 and a facsimile machine 44. Station 100 need only have a facsimile machine 122. Printer 42 enables the patient to receive prescriptions, and itemized bill statements generated by the medical practitioner located in station 100. Patient history forms, and other written information is conveyed using facsimile machines 44 and 122. Located in practitioner's station 100 is a video recorder 124 that records the session between the patient and doctor for future reference, auditing and security purposes.

Patient's station 20 is equipped with a variety of diagnostic devices that measure and monitor parameters related to health that aid the medical practitioner in making an accurate diagnosis of the patient. Representative of these diagnostic tools include a blood pressure monitor 46, a thermometer 48, and a heart rate monitor 50. It is recognized that other diagnostic tools could be incorporated within station 20 without departing from the spirit and scope of the present invention. Such tools include, but are not limited to, devices that measure one's weight, respiratory rate, and oximetry conditions. Data gathered from blood pressure monitor 46, thermometer 48, and heart rate monitor 50 is displayed on terminal 118 in station 100. An adjustable light 52, located in station 20 is controlled by the practitioner in station 100 via keyboard 118. Adjustable light 52 permits the practitioner to focus light upon areas of the patient that require more attention, such as the mouth or ears. Preferably the physician at the practitioner's station 100 would also have the capability to "zoom" the lens of the video camera 24 onto the patient for closer examination.

To ensure the identity of the patient who seeks medical attention, station 20 is equipped with a frame 54 dimensioned to receive an insurance card, driver's license or other types of identification cards having similar dimensions. Frame 54 which extends a slight distance from front wall 56.

Recessed within station 20 and directed towards frame 54 is a video camera 58. A patient desiring treatment will be requested to show proof of identity. At that time, the patient will insert an identification card within frame 54. Video camera 58, or alternatively a scanner, will then create a video image of the identification card placed within frame 54. The video image is then converted to a still image by CPU 22, using conversion techniques commonly employed in the art. Thereafter, the still image is transmitted to station 100 via communications link 150 and displayed on terminal 118.

After identification is established, the patient is requested to select a mode of payment. At this point there are several alternatives available to the patient. If the patient has health insurance or is a member of a health management organization, and wishes to pay through that organization or insurance company, proof of membership in the form of a card is placed within frame 54 as detailed above. The information detailed on that card will be forwarded to practitioner's station 100 where it will be further processed. Alternatively, the patient may wish to pay using a credit card. To accommodate this mode of payment, station 20 is equipped with a credit card machine 60 and electronic signature device 62. With this option, a patient runs the credit card through machine 60. Credit data collected from the card is transmitted to practitioner's station 100. Prior to the end of the session, the practitioner will transmit an itemized bill which will appear on terminal 38 of practitioner's station 100. If the patient agrees with the charges, the patient signs the bill using electronic signature device 62. Thereafter, a paper copy of the bill is sent to station 20 via printer 42.

Another mode of payment which may be used by the patient to pay for services rendered is as follows: The manager or owner of the premises where patient's station 20 is located, such as a pharmacy, for a fee, will provide the patient with an account or voucher number prior to the initiation of services with the medical practitioner. Upon requesting the attention of the practitioner, the patient will be prompted to input the account number using keyboard 36. After services have been rendered, the retailer or owner is billed under the given account number.

Communications link 150, which provides the connection between station 20 and station 100 may be any system normally employed within the art of communication networking which is capable of simultaneously transmitting data, video and audio signals between station 20 and station 100. Such communications links include, but are not limited to, data modems and standard or dedicated telephone lines, fiber optic cable transmission, satellite transmission, or a combination thereof.

Turning now to FIG. 2 there is shown a flow chart depicting the major steps that occur during a session between patient and practitioner using medical communication system 10. Activation of patient station 20 is made by requesting services of the medical practitioner. Once a request for services has been made, the patient will be prompted by a message appearing on terminal 38 to insert an identification card within frame 54. Thereafter, the patient will be requested to choose a form of payment. As detailed above, the patient may choose to pay via a credit card, insurance program or by a prepaid account number. Once a mode of payment is established, terminal 38, driven by CPU 22 will "interview" the patient by asking preliminary questions that facilitate an accurate diagnosis. Once these questions are completed, video and auditory connections between station 20 and 100 are initiated. The patient will then be requested to validate the answers to the previously asked questions. This is accomplished using electronic signature device 62. In lieu of a computer prompted questionnaire, the patient may be asked the same preliminary questions by a nurse or other medical assistant. The medical assistant types the answers to the questions using keyboard 116. Once the preliminary questions have been answered they are sent via printer 42 for review by the patient. Thereafter, the patient signs the paper copy and transmits it to station 100 using facsimile 44.

At this point, the patient is interviewed by a nurse or other medical assistant. This interview normally includes the collection of vital signs using blood pressure monitor 46, thermometer 48, and heart rate monitor 50. Thereafter, the patient is interviewed and diagnosed by the medical practitioner. Immediately prior to the end of the session the patient is sent via facsimile 44, a statement of the charges associated with the diagnosis and a prescription statement for any medications prescribed by the practitioner.

Several examples of the use of the present system have been given and suggested in the foregoing description. However, additional examples will be given below.

EXAMPLE 1

A patent with arthritis has seen a doctor and been given a prescription for a pain reliever. The patient wants to have the prescription refilled. The patent goes directly to a pharmacy equipped with the present invention where he contacts the doctor's office. The nurse at that office asks the patient routine questions to obtain the answers the doctor would need in order to authorize a refill of the prescription. The new prescription is sent to the patient by facsimile and he fills it at the pharmacy.

EXAMPLE 2

A medical specialist with a national reputation and living west of Denver at his home equipped with the present invention, is contacted by a small clinic in rural Montana. The doctor examines the patient in accordance with the present invention and recommends a course of treatment to the patient and his attending physician.

EXAMPLE 3

A parent takes a sick child to a kiosk at a nearby shopping area late on a Saturday night. A physician on duty at a hospital in the area examines the child according to the present invention and recommends an interim course of treatment for the child until regular business hours for the child's pediatrician resume Monday. A copy of the record of the examination and the diagnosis and treatment are sent by facsimile to the pediatrician.

EXAMPLE 4

A doctors' group in a rural state set up kiosks with patient's stations in a large number of small rural towns where that are underserved by medical practitioners. Local residents go to the kiosks for examination according to the present invention and, only when warranted, travel to the practitioner's location if additional diagnosis and treatment is needed. Some of the kiosks are manned by nurses who can facilitate the examinations and give injections, treat minor burns, draw blood, etc.

It will be apparent to those skilled in the art that many modifications and substitutions can be made to the preferred embodiment just described without departing from the spirit and scope of the invention as defined in the appended claims.

What is claimed is:

1. A system for examination of a patient by a medical practitioner comprising:

a first station;

a second station spaced apart from said first station;

first communicating means in said first station;

second communicating means in said second station;

means for connecting said first and said second communicating means so that said patient and said practitioner can transfer information between said first and said second stations when said patient is at said first station and said practitioner is at said second station;

means carried by said first station for verifying the identity of said patient; and means carried by said first station for establishing a mode of payment for said examination, wherein said first station is operated by a retailer and wherein said patient has an account number issued by said retailer and wherein said establishing means further comprises means carried by said second station for billing said retailer under said account number.

2. The system as recited in claim 1, further comprising means carried by said first station for measuring the blood pressure of said patient, said blood pressure measuring means being in electrical connection with said connecting means.

3. The system as recited in claim 1, further comprising means carried by said first station for measuring the temperature of said patient, said temperature measuring means being in electrical connection with said connecting means.

4. The system as recited in claim 1, further comprising means carried by said first station for measuring the heart rate of said patient, said heart rate measuring means being in electrical connection with said connecting means.

5. The system as recited in claim 1, wherein said verifying means further comprises means carried by said first station for generating an image of at least one identification card, said generating means being in electrical connection with said connecting means.

6. The system as recited in claim 1, wherein said verifying means further comprises:

a frame mounted in said first station, said frame dimensioned to receive at least one identification card carried by said patient;

a video camera carried by said first station, said video camera producing a video image of said at least one identification card; and means for converting said video image to a still image, said converting means being in electrical connection with said connecting means.

7. The system as recited in claim 1, wherein said establishing means further comprises:

means carried by said first station for accepting a credit card, said accepting means being in electrical connection with said connecting means; and an electronic signature device carried by said first station, said electronic signature device being in electrical connection with said connecting means.

8. The system as recited in claim 1, wherein said first communicating means further comprises first means for generating video images and first means for receiving video images, said first means for receiving and said first means for generating being in electrical connection with said connecting means, and wherein said second communicating means further comprises a second means for generating video images and a second means for receiving video images, said second means for generating and said second means for receiving being in electrical connection with said connecting means so that said patient and said practitioner can transfer video images between them when said patient is at said first station and said practitioner is at said second station.

9. A system for examination of a patient by a medical practitioner comprising:

a first station;

a second station spaced apart from said first station;

first communicating means in said first station;

second communicating means in said second station;

means for connecting said first and said second communicating means so that said patient and said practitioner can transfer medical information between said first and second stations when said patient is at said first station and said practitioner is at said second station;

means carried by said first station for generating an image of at least one identification card carried by said patient, said generating means being in electrical connection with said connecting means; and means carried by said first station for accepting a credit card, said accepting means being in electrical connection with said connecting means; and an electronic signature device carried by said first station, said electronic signature device being in electrical connection with said connecting means, wherein said first station is operated by a retailer and wherein said patient has an account number issued by said retailer and wherein said establishing means further comprises means carried by said second station for billing said retailer under said account number.

10. The system as recited in claim 9, further comprising:

means carried by said first station for measuring the temperature of said patient, said temperature measuring means being in electrical connection with said connecting means; and means carried by said first station for measuring the blood pressure of said patient, said blood pressure measuring means being in electrical connection with said connecting means.

11. The system as recited in claim 9, further comprising means carried by said first station for measuring the heart rate of said patient, said heart rate measuring means being in electrical connection with said connecting means.

12. The system as recited in claim 9, wherein said generating means further comprises:

a frame mounted in said first station, said frame dimensioned to receive at least one identification card carried by said patient;

a video camera carried by said first station, said video camera producing a video image of said at least one identification card; and means for converting said video image to a still image, said converting means being in electrical connection with said connecting means.

13. The system as recited in claim 9, wherein said first communicating means further comprises first means for generating video images and first means for receiving video images, said first means for receiving and said first means for generating being in electrical connection with said connecting means, and wherein said second communicating means further comprises a second means for generating video images and a second means for receiving video images, said second means for generating and said second means for receiving being in electrical connection with said connecting means so that said patient and said practitioner can transfer video images between them when said patient is in said first station and said practitioner is in said second station.

* * * * *